(12) United States Patent
Loftus

(10) Patent No.: US 9,770,405 B1
(45) Date of Patent: Sep. 26, 2017

(54) BIOCOMPATIBLE CAPSULES AND METHODS OF MAKING

(71) Applicant: The United States of America as Represented by the Administrator of the National Aeronautics & Space Association (NASA), Washington, DC (US)

(72) Inventor: David J. Loftus, Palo Alto, CA (US)

(73) Assignee: The United States of America as Represented by the Administrator of NASA, Washington, DC (US)

( * ) Notice: Subject to any disclaimer, the term of this patent is extended or adjusted under 35 U.S.C. 154(b) by 755 days.

(21) Appl. No.: 13/645,284

(22) Filed: Oct. 4, 2012

Related U.S. Application Data

(60) Provisional application No. 61/662,870, filed on Oct. 5, 2011.

(51) Int. Cl.
*A61K 9/00* (2006.01)
(52) U.S. Cl.
CPC ...................................... *A61K 9/00* (2013.01)
(58) Field of Classification Search
CPC .................................................. A61K 9/0092
See application file for complete search history.

(56) References Cited

U.S. PATENT DOCUMENTS

| | | | |
|---|---|---|---|
| 6,979,709 B2* | 12/2005 | Smalley et al. | 524/495 |
| 7,070,923 B1 | 7/2006 | Loftus | |
| 7,105,596 B2 | 9/2006 | Smalley et al. | |
| 7,135,172 B1 | 11/2006 | Loftus et al. | |
| 7,618,647 B2 | 11/2009 | Weber et al. | |
| 2007/0254024 A1* | 11/2007 | Cade et al. | 424/451 |

OTHER PUBLICATIONS

Cui et al., J. Mater. Chem. A, 2013, 1, 13984.*

* cited by examiner

*Primary Examiner* — Robert Cabral
(74) *Attorney, Agent, or Firm* — Christopher J. Menke; Robert M. Padilla; Mark P. Dvorscak

(57) ABSTRACT

Embodiments of the invention include capsules for containing medical implants and delivery systems for release of active biological substances into a host body. Delivery systems comprise a capsule comprising an interior enclosed by walls, and a source of active biological substances enclosed within the capsule interior, wherein the active biological substances are free to diffuse across the capsule walls. The capsule walls comprise a continuous mesh of biocompatible fibers and a seal region where two capsule walls overlap. The interior of the capsule is substantially isolated from the medium surrounding the capsule, except for diffusion of at least one species of molecule between the capsule interior and the ambient medium, and prevents cell migration into or out of the capsule. Methods for preparing and using the capsules and delivery systems are provided.

11 Claims, 10 Drawing Sheets

BIOCOMPATIBLE CAPSULES AND METHODS OF MAKING

CROSS REFERENCE TO RELATED APPLICATIONS

This application claims priority from U.S. Provisional Application Ser. No. 61/662,870, filed Oct. 5, 2011, entitled "Method for Formation and Manufacture of Carbon Nanotube Mesh Bucky Paper Capsules for Transplantation of Cells and Tissue and Implantation of Medical Devices" which is incorporated by reference herein in its entirety.

ORIGIN OF THE INVENTION

The invention described herein was made by an employee of the United States Government and may be manufactured and used by or for the Government of the United States of America for governmental purposes without the payment of any royalties thereon or therefor.

FIELD OF THE INVENTION

One or more embodiments of the present invention relate to medical devices and methods of medical treatment of disease. Other pertinent fields of the invention include drug delivery systems, transplant medicine, cell therapeutics and synthetic biology.

BACKGROUND

Transplantation of cells and tissues from one human to another is limited by the host immune system, which identifies and rejects non-host cells and tissues with high efficiency. One strategy for avoiding or surmounting this barrier is to enclose the cells in a "cage" that provides a biological shield (an "immune shield") that prevents the transplanted cells and tissues from being rejected by the host immune system. This strategy has application in endocrinology (e.g., islet cell transplantation), gene therapy (transplantation of cells to provide a missing protein or to replace a dysfunctional protein), immune therapy, or other biological therapy (transplantation of cells to provide specific active biological molecules, such as immunoglobulins, cytokines, immune regulators or biological response modifiers). Such a system could also provide a micro-environment, within a human or other host body, for tissue engineering, to allow for differentiation of cells or assembly of tissue structures with two-dimensional or three-dimensional architecture, or the formation of nascent organs, for subsequent use in the host or elsewhere.

Immune shielding may also serve as an important strategy for preventing immune rejection of implantable medical devices that range in size from ultra-small scale nanoparticles and nanoprobes to large scale macroscopic devices. The strategy of immune shielding allows use of a wider range of materials in the construction of implantable medical devices than would otherwise be possible because of the presence of the host immune system and therefore the potential for unwanted immune system responses.

Many materials have been proposed as immune shields, including specially treated biological and non-biological materials, silicon, ceramics, synthetic polymers and other non-organic materials. As a rule, these foreign materials tend to provoke an immune response in the host body, which has limited development in this field. Another phenomenon associated with transplantation of foreign materials into a host is localized scar formation ("fibrotic capsule formation") and/or obstruction of pores in the foreign material. The presence of pores is required in most biological applications for efficient transfer of nutrients, gases and other biological factors into the interior of the cage, and efficient transfer of waste products, metabolites and secreted substances from inside the capsule to outside the cage.

What is needed is a biocompatible material that can be formed into a "cage" or similar structure for containing cells or tissue that prevents or limits access by the host immune system to the foreign cells or tissue. The capsule material should allow the cells and/or tissue to be maintained in a live and functioning state; and in some cases, should permit the cells and/or tissue to carry out normal (physiological) or specially engineered sensing functions and/or normal (physiological) or specially engineered secretory functions. The capsule material itself should not provoke (or should limit significantly) an immune response in the host system. The capsule material itself should not elicit (or should limit significantly) scar formation in the host that, together with an immune response, could lead to obstruction of the pores of the capsule material. The capsule material itself should resist protein deposition that, together with scar formation or an immune response, could lead to obstruction of the pores. Preferably, the material should be flexible and sufficiently resilient to withstand the forces that may be involved in surgical implantation or transplantation and other forces that may be present in the host environment. The material should be configurable into a variety of geometric shapes, to optimize transport of substances across the capsule and to promote the maintenance of cells and/or tissues.

U.S. Pat. No. 7,070,923 to Loftus describes the use of carbon nanotube Bucky paper for the transplantation or implantation of cells and/or tissues or medical devices, wherein containers for cells and/or tissues or medical devices are fabricated from multiple layers of flat pieces of carbon nanotube Bucky paper in a sandwich configuration. Three-dimensional structures made from flat pieces of carbon nanotube Bucky paper, such as tubes made by rolling up flat pieces of carbon nanotube Bucky paper, or rolls of Bucky paper with multiple spiral layers are also disclosed. However, the formation of 3-dimensional structures from flat pieces of Bucky paper requires potentially time-consuming and potentially labor intensive procedures to manipulate the flat pieces of Bucky paper. The formation of 3-dimensional structures from flat pieces of Bucky paper also requires seams between individual pieces of Bucky paper, either "edge to edge" seams or "overlapping seams," and, in some cases, the use of additional materials such as suture or other ligature to close the seams. These seams may be undesirable, because they may constitute points or regions of structural weakness of the Bucky paper containers, which could result in rupture of the Bucky paper containers. In addition, the seams are undesirable because they may result in leakage or migration of the cells and/or tissue or medical devices from inside the Bucky paper containers to outside the Bucky paper containers. In addition, the seams may serve as points of entry of host immune system cells to the interior of the Bucky paper containers, which could result in an undesirable immune system response to the cells and/or tissues or medical devices contained therein.

U.S. Pat. No. 7,618,647 to Weber describes uses of Bucky paper on medical implants such as stents. The Bucky paper is applied by wrapping the stents with Bucky paper and securing the paper with clamps, sewing or glue. Nonplanar Bucky paper can allegedly be formed using a cylindrical or tubular filter, or by forming a filter into a pouch shape.

Weber states that an implant can be placed inside the pouch and additional Bucky paper formed on top to enclose the implant. However, no method of forming Bucky paper on top of a pouch containing an implant is provided, and the methods otherwise disclosed for forming Bucky paper in situ would not be operable to close the top of a pouch in a leak-proof manner. Spraying techniques are also described where a suspension of nanotubes is sprayed onto an implant, the solvent dried and the nanotubes compressed onto the implant; however spraying, drying and compressing would damage the structure of the finished capsule, disrupting its integrity. Weber fails to disclose any means of creating a leak-proof capsule or enclosure for any device or bioactive structure or material.

SUMMARY OF THE INVENTION

Embodiments of the invention include capsules for containing medical implants and delivery systems for release of active biological substances into a host body. Delivery systems comprise a capsule comprising an interior enclosed by walls, and a source of active biological substances enclosed within the capsule interior. The capsule walls comprise a continuous mesh of biocompatible fibers and a seal region where two capsule walls overlap. The interior of the capsule is substantially isolated from the medium surrounding the capsule, except for diffusion of at least one species of molecule between the capsule interior and the ambient medium. The seal region where the capsule walls overlap comprises a mesh which is sufficiently continuous to prevent cell migration into or out of the capsule.

In some embodiments, the source of active biological substances is a plurality of cells, wherein the plurality of cells releases the one or more active biological substances such that the one or more active biological substances are free to diffuse across the capsule walls.

In some embodiments, the source of active biological substances is a composition comprising one or more active biological substances, wherein the composition releases the one or more active biological substances such that the one or more active biological substances are free to diffuse across the capsule walls, i.e., from inside the capsule to outside of the capsule. The composition can be a sustained release composition.

In some embodiments, the source of active biological substances is a medical device providing the controlled release of one or more active biological substances, wherein the composition releases the one or more active biological substances such that the one or more active biological substances are free to diffuse across the capsule walls.

The biocompatible fibers can comprise carbon nanotubes (single-walled nanotubes or multi-walled nanotubes), carbon fibers, carbon nanofibers, graphene, graphene flakes, graphene fragments, graphene fibers, or polysaccharides (e.g., bacterial cellulose). The fibers can be randomly oriented or substantially oriented in the capsule walls. The capsule can comprise fibers of varying composition in one or more distinct layers in the capsule walls. The capsules can incorporate beads into one or more distinct layers in the capsule walls. The capsule can further comprise fibers or beads disposed in the interior of the capsule. The capsule walls have a thickness in a range of 1-100 μm and an area density in a range of 420-1500 μgm/cm$^2$.

In some embodiments, medical devices encapsulated by a capsule are provided, wherein the capsule encapsulates the medical device such that the medical device does not provoke a response from the host immune system when implanted into a host body. The capsule comprises biocompatible fibers and forms an interior enclosed by walls. The interior of the capsule is substantially isolated from the medium surrounding the capsule, except for diffusion of at least one species of molecule between the capsule interior and the ambient medium.

In some embodiments, methods are provided for preparing a biocompatible capsule. The methods can comprise providing a perforated mold, immersing the perforated mold into a suspension of biocompatible fibers in a suspending medium, withdrawing the suspending medium through the perforated mold such that the fibers form a tangled mesh around the outside of and conform to the shape of the perforated mold, and removing the perforated mold to produce a biocompatible capsule component, and sealing the capsule. The sealing comprises forming at least one region of overlap where two regions of capsule wall are in intimate contact, and pressing the two regions of capsule wall together such that the capsule wall surfaces are bound by van der Waals forces and/or entanglement of the biocompatible fibers. When sealed, the capsule interior is substantially isolated from the medium surrounding the capsule, except for diffusion of at least one species of molecule between the capsule interior and the ambient medium.

The methods can further comprise providing a plurality of molds to prepare a plurality of capsule components, and assembling the plurality of capsule components to form an enclosed 3-dimensional capsule. The suspending medium can be withdrawn by applying positive pressure to the outside of the perforated mold or by applying negative pressure to inside of the perforated mold.

The methods can further comprise inserting a plurality of cells into the capsule before assembling the capsule components together. The methods can further comprise inserting a medical device into the capsule before assembling the capsule components together.

The methods can further comprise inserting a source of one or more active biological substances into the capsule before assembling the capsule components together. The active biological substance can include pharmaceutically active agents, chemotherapeutic agents, radio-labeled agents, peptides, proteins, growth factors, cytokines, growth inhibitors, polynucleotides, and the like, without limitation.

In some embodiments, the source of active biological substances is a plurality of cells, wherein the plurality of cells releases the one or more active biological substances such that the one or more active biological substances are free to diffuse across the capsule walls.

In some embodiments, the source of active biological substances is a composition comprising one or more active biological substances, wherein the composition releases the one or more active biological substances such that the one or more active biological substances are free to diffuse across the capsule walls. The composition can be a sustained release composition.

In some embodiments, the source of active biological substances is a medical device providing the controlled release of one or more active biological substances, wherein the composition releases the one or more active biological substances such that the one or more active biological substances are free to diffuse across the capsule walls.

The biocompatible fibers can comprise carbon nanotubes, carbon fibers, carbon nanofibers, graphene, graphene flakes, graphene fragments, graphene fibers, or polysaccharides (e.g., bacterial cellulose). The methods can further comprise orienting the fibers as the capsule components are formed. The methods can further comprise incorporating different fibers into one or more distinct layers as the capsule components are formed. The methods can further comprise incorporating beads into one or more distinct layers as the capsule components are formed. The methods can further comprise incorporating fibers into the interior of the capsule components to form an interior scaffold before sealing the capsule. The methods can further comprise incorporating beads into the interior of the capsule before sealing the capsule.

In some embodiments, delivery systems for release of active biological substances are provided comprising a source of active biological substances enclosed within a capsule made according to methods disclosed herein.

DETAILED DESCRIPTION OF THE INVENTION

Figure 1:
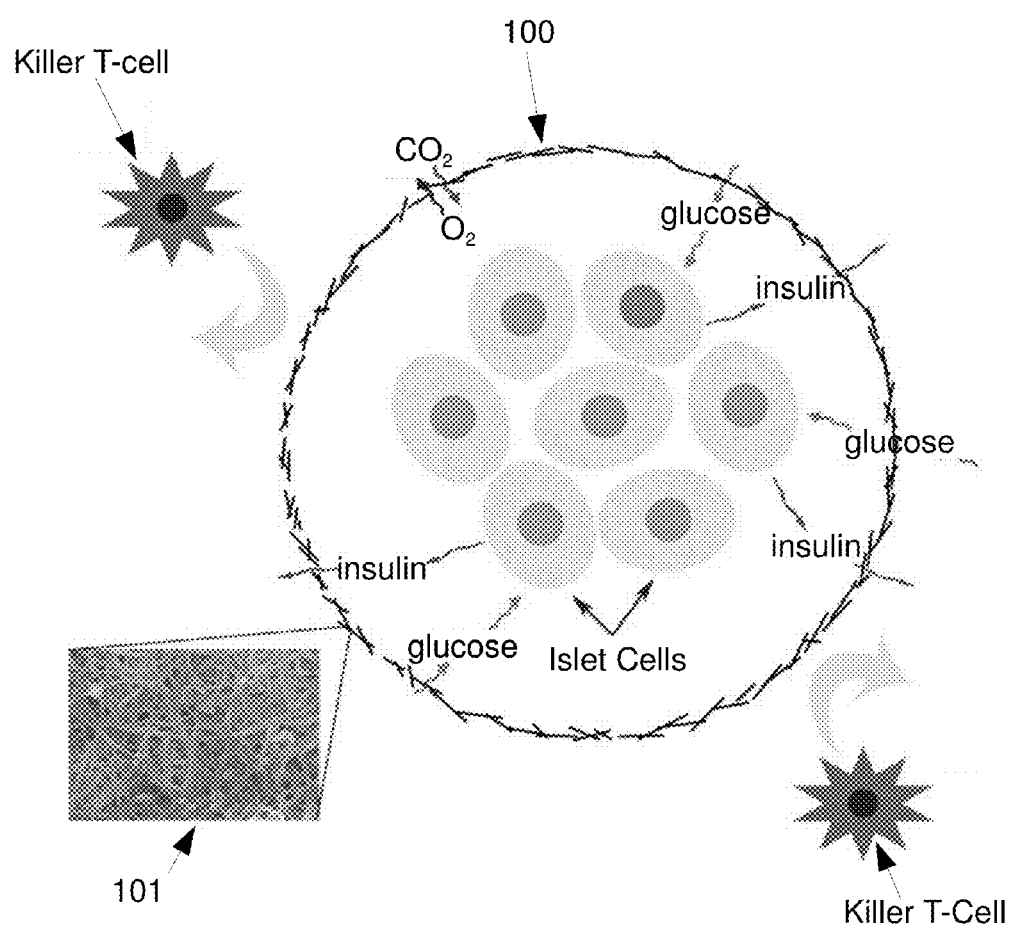
FIG. 1 illustrates an embodiment of a capsule containing islet cells.

Before the present invention is described in detail, it is to be understood that unless otherwise indicated this invention is not limited to specific materials, polymers or devices. It is also to be understood that the terminology used herein is for the purpose of describing particular embodiments only and is not intended to limit the scope of the present invention.

It must be noted that as used herein and in the claims, the singular forms "a," "and" and "the" include plural referents unless the context clearly dictates otherwise. Thus, for example, reference to "a polymer" includes two or more polymers, and so forth.

Where a range of values is provided, it is understood that each intervening value, to the tenth of the unit of the lower limit unless the context clearly dictates otherwise, between the upper and lower limit of that range, and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention. Where the modifier "about" is used, it is understood that the stated quantity may vary by up to ±10%.

I. Definitions and Overview

As used herein, the term "active biological substance" (or "ABS") refers to molecules that bind to receptors or act as pharmacologically active agents and affect some property of biological tissues, without limitation. An ABS can include hormones, peptides or proteins (enzymes, ligands, cytokines, transcription factors, etc.), pharmaceutical agents, antibodies, polynucleotides (interfering RNAs, DNA), prohormones, or precursors to ABS that become activated in the host body, and the like without limitation. An ABS also includes labeled substances, such as fluorescent labels, spin labels, radioactive labels, and so forth. An ABS also includes drug-ABS conjugates of drugs or cytotoxic agents (e.g., maytansine, etc.) or fusion protein-ABS constructs.

As used herein the term "ambient medium" refers to the environment surrounding a capsule. When implanted into a host body, the ambient medium can include blood, interstitial fluids and extracellular matrix, and the like.

As used herein, the term "beads" refers to beads, microparticles, or nanoparticles typically spherical or near so.

As used herein, the term "biocompatible" refers to the property of being relatively inert with respect to provoking a response from a host immune system.

As used herein, the term "capsule" refers to a container comprising biocompatible fibers and enclosing a 3-dimensional volume which is sealed by van der Waals interactions and/or entanglement of the biocompatible fibers of surfaces in intimate contact. The biocompatible fibers interact and bond without glue, stitching, clamps or other closing techniques.

As used herein, the term carbon nanotube ("CNT") encompasses both single wall nanotubes or multiwalled nanotubes.

As used herein, the term "Bucky paper" refers to a mesh prepared from CNTs. The preparation and use of Bucky paper is described in U.S. Pat. Nos. 7,070,923 and 7,135,172 to Loftus, incorporated by reference herein.

As used herein, the term "substantially isolated" refers to the property of preventing the passage of cells across the walls of the capsule, while allowing the passage of at least one species of molecule between the capsule interior and the ambient medium.

Embodiments of the present invention utilize methods for creating 3-dimensional containers or capsules made of a biocompatible fibrous mesh. The novel methods improve upon the methods and constructs prepared using the methods described in U.S. Pat. Nos. 7,070,923 and 7,135,172 to Loftus. Advantageously, the methods do not rely on manipulation of flat pieces of Bucky paper, and do not require stitching to assemble into a sealed container. The improved methods provide for more efficient manufacture of containers, largely eliminate the requirement for seams between individual pieces of Bucky paper, and increase the range of possible shapes of the Bucky paper containers. In addition, the methods make it possible to control the orientation of the individual CNTs of the meshwork to tailor the meshwork properties to specific applications, as well as to incorporate other components into the container structure during the manufacturing process.

Compared to both the Loftus patents cited above and U.S. Pat. No. 7,618,647 to Weber, embodiments of the invention provide new methods of sealing capsules and similar enclosures without using any material other than the biocompatible fibers from which the walls of the capsules are made. The sealing is provided both to protect the contents placed in the enclosure from attack by the host immune system and to prevent the contents from leaking out into the host. In one aspect, a method is provided for creating fibrous mesh from suspensions of CNTs or other biocompatible fibers to form three-dimensional structures, such as hollow tubes, cylinders closed at one end, as well as more complex shapes, for the purpose of providing containers for cells and/or tissues or medical devices, for the purpose of transplanting or implanting the cells and/or tissues into a host. The methods can also provide containers for medical devices to be implanted into a host.

The capsules formed from CNTs and carbon nanofibers are biocompatible and nonthrombogenic, and can conceivably be placed into contact with blood, i.e., in a blood vessel, if suitably sized. The biocompatibility of the capsule material (CNT meshwork) was demonstrated in a rabbit model. A flat portion of a capsule wall (CNT meshwork) was prepared by the vacuum filtration method and sterilized by gamma irradiation. The portion was implanted into the sub-retinal space of an albino rabbit. After 1 week, the implant site showed no signs of acute inflammation, by direct observation.

Some embodiments incorporate beads which can be used with externally applied radiation to trigger or otherwise signal the capsules. Some embodiments include CNTs or other filaments inserted into the interior of the capsule. Methods for achieving preferential orientation of the CNTs (or other filaments) within the capsule wall, as well as the use of a variety of CNT lengths or filament lengths are also described.

II. Delivery Systems and Capsules

Embodiments of the present invention provide capsules for containing medical implants and delivery systems for release of active biological substances into a host body. The delivery systems comprise a capsule comprising an interior enclosed by walls, and a source of active biological substances enclosed within the capsule interior. The capsule walls comprise a continuous mesh of biocompatible fibers and a seal region where two capsule walls overlap. Sealing of the capsule is achieved by van der Waals interaction and/or entanglement of the biocompatible fibers of surfaces in intimate contact. The biocompatible fibers interact and bond without glue, stitching, clamps or other closing techniques. Discontinuity can exist where the walls overlap, but interdigitation of fibers occurs which results in a mesh which is sufficiently continuous to prevent cell migration from the capsule to the ambient medium or from the ambient medium into the capsule.

The interior of the capsule is substantially isolated from the medium surrounding the capsule, except for diffusion of at least one species of molecule between the capsule interior and the ambient medium. Where the capsule is used for growth, differentiation, non-differentiation or transplantation of cells and/or tissue, the capsule porosity can be selected to allow passage of some molecules and to exclude passage of other molecules. Where the capsule is used for containing cells and/or tissue, the capsule walls preferably have a selected porosity that permits exchange of one or more selected molecules between the capsule interior and exterior, such as $O_2$, $CO_2$, amino acids, glucose, peptides and small proteins.

The capsule may also be used for secretion of one or more active biological substances ("ABS") at one or more controlled rates, from the capsule interior to the capsule exterior, thereby providing a delivery system for the one or more ABS. In some embodiments, the source of active biological substances is a plurality of cells, wherein the plurality of cells releases the one or more active biological substances such that the one or more active biological substances are free to diffuse across the capsule walls. In some embodiments, the source of active biological substances is a composition comprising one or more active biological substances, wherein the composition releases the one or more active biological substances such that the one or more active biological substances are free to diffuse across the capsule walls. The composition can be a sustained release composition. In some embodiments, the source of active biological substances is a medical device providing the controlled release of one or more active biological substances, wherein the composition releases the one or more active biological substances such that the one or more active biological substances are free to diffuse across the capsule walls.

As an example, where the patient has a non-functioning or poorly functioning pancreas or thyroid, a substitute tissue, organ fragments or cells from another human, or even from another species, may be enclosed in the capsule which acts as an immune shield within the patient's body. The capsule protects the non-self cells and/or tissue from an immune reaction by the patient's body but allows secretion of the desired ABS (e.g., insulin or thyroid hormone) into the patient's body adjacent to the location of the capsule. The rate at which the ABS is secreted into the patient's body is determined by the intrinsic sensing function of the cells and/or tissue (e.g., for insulin secreting cells and/or tissue, sensing the concentration of glucose) and is not limited by the capsule, if the capsule is sufficiently porous.

One embodiment of an insulin delivery system 100 is illustrated in FIG. 1 (shown schematically in cross-section). A capsule containing islet cells is prepared and implanted in a patient needing treatment for diabetes. The islet cells are viable and nourished by the patient's body. Immune cells (shown labeled as "Killer T-cell") and islet cells cannot penetrate the capsule walls. The islet cells are not in contact with the host immune system and therefore do not generate and/or are protected from the host immune response. However, small molecules such as glucose, insulin, $CO_2$ and $O_2$ are able to diffuse across the capsule walls.

Similarly, additional delivery systems can be envisaged, such as thyroid tissue for delivery of thyroid hormone, genetically engineered cells for delivery of specific proteins such as clotting factors, cytokines, antibodies, without limitation.

A capsule can also support implantation into a host body of a biological insert that is a plurality of cells genetically engineered to possess a specialized function. The activity associated with this function is controlled by an agent that can regulate specific gene expression or other specific biological activity in the biological insert and thus provide the specialized function. For some applications, the biological insert is implanted with the specialized function turned off (inactive). This insert is maintained in the host body in a live state until the specialized function is needed, at which point the biological insert is activated, for example, by administration of a chemical or biological triggering agent. When the specialized function is no longer needed, a second triggering agent is administered to deactivate the insert or expression of the specific gene or specific biological activity of the insert. Alternatively, a third triggering agent can be administered to trigger death or its equivalent in the biological insert. This approach may have particular usefulness in providing medical care to military personnel or to astronauts on long space flights, where access to conventional medical care is limited.

Figure 2:
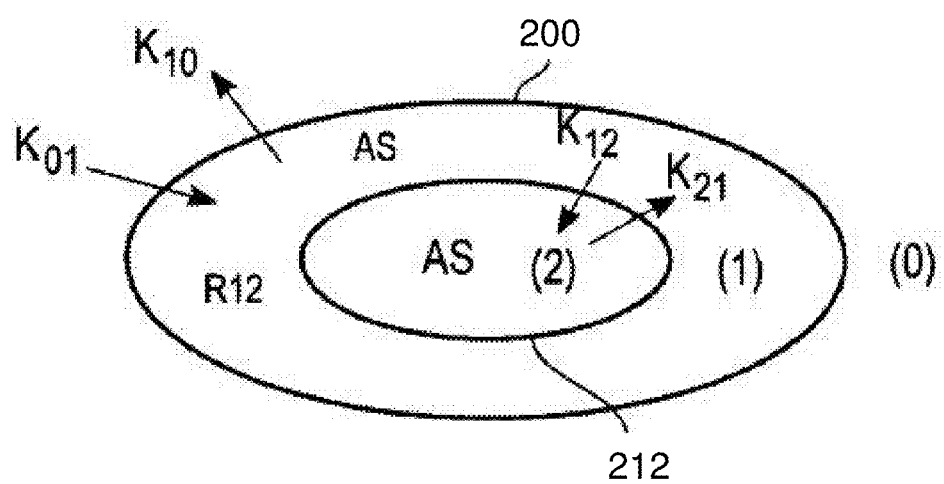
FIG. 2 illustrates one embodiment of a delivery system.

In some embodiments, the capsule can be used as a delivery system to provide release of an ABS into a host body by placing the ABS directly into the capsule (i.e., without using cells and/or tissue to secrete the ABS). The ABS can be provided in solution or as a solid. The ABS can be provided in a sustained release composition, providing release of the ABS into the capsule for an extended period of time. For example, the sustained release composition can provide a sustained release of an ABS from a capsule for a year or more.

Where an ABS is passively released from a capsule, one concern is the inevitable decrease in rate of release as the concentration of the ABS within the capsule decreases. This decrease in rate can be controlled, although not eliminated, by enclosing a second capsule 212 of the ABS, with a second initial ABS concentration $c_2(t=0)$, within a first, larger capsule 200 of the active biological substance, having an initial ABS concentration $c_1(t=0)$, which is in turn immersed in an ambient medium, having a relatively unvarying ABS concentration $c_0(t=0)$, as illustrated in FIG. 2. Preferably, the concentration values satisfy $c_0(t=0) \ll c_1(t=0) \ll c_2(t=0)$. The rate constants for diffusion of the ABS from the first capsule to the second capsule, and from the second capsule to the first capsule, have the respective values $k_{12}$ and $k_{21}$, where these two values may be equal or unequal. The rate constants for diffusion of the ABS from the first capsule to the ambient-medium, and from the ambient medium to the first capsule, have the respective values $k_{10}$ and $k_{01}$, where these two values may be equal or unequal. Preferably, $k_{10} < k_{21}$. The capsule material for the first capsule can be formed from CNT fibers or another material that serves as an immune shield; the capsule material for the second capsule may be an immune shield material or another suitable material that may not provide immune shielding. By suitable choices of ratios of the parameters, the rate of decrease of the resulting secretion rate $k_{10} \cdot c_1(t)$ from the first capsule to the ambient medium is reduced relative to the rate of decrease that would occur if the first capsule, but not the second capsule, is present. The rate of decrease of the resulting passive release, $k_{10} \cdot c_1(t)$, from the first capsule to the ambient medium may be further reduced by provision of N capsule, numbered $n=1, \ldots, N$ ($N \geq 3$), with capsule number n being larger than and enclosing capsule number n+1 ($n=1, \ldots, N-1$). This approach may be used for a capsule or for a first capsule made of any other material that serves as an immune shield. A stand-alone first capsule 200 can also be used for secretion, if the decrease in passive release rate for the active biological substance ABS from the pocket is not a great concern, or if the ABS is poorly soluble and hence can maintain a relatively constant dissolution profile with time.

A capsule may also be used to sense the presence or monitor the concentration of one or more selected substances in an ambient medium surrounding part or all of the capsule. In this situation, the capsule walls are modified, as appropriate, to allow or promote transfer of the substance across the capsule wall, from the ambient medium to the capsule interior. A chemical substance or device, which reacts and undergoes a chemical or physical reaction, is located within the capsule interior. The presence or intensity of this resulting reaction within the capsule is monitored to determine the presence or the concentration of the substance in the ambient medium. For example, a glucose sensing device can be enclosed within a capsule and implanted in a host body. The glucose sensing device can monitor the interstitial fluids surrounding the capsule for the concentration of glucose, and a signal can be transmitted out of the host body to a receiver for recording the information. Similar applications to other sensing functions will immediately be understood by those skilled in the art.

A capsule can also enclose a mechanical, electromechanical, electronic or physical medical device and provide protection from the host immune system. There is no particular size limit to the capsules that can be formed, and the capsules can be sized large enough to enclose miniaturized medical devices such as osmotic pumps for drug delivery (e.g., ALZET® Osmotic Pumps) or larger medical devices such as pacemakers or microfluidic delivery systems. In addition, the capsule can be formed as a long thin tube for containing a medical device having a long and thin shape, for example, catheters and guidewires. The capsule provides the added advantage of being nonthrombogenic and so provides protection against clot formation upon exposure of the host body to the medical device.

The medical device may provide or transform a selected chemical or a selected chemical signal, optical signal, electronic signal, electromagnetic signal, ultrasound signal, mechanical signal or other signal within the capsule, for subsequent use inside or outside the capsule, and may be a nano-device (with a device diameter of the order of nanometers to microns) or may be a larger device, referred to here as a macroscopic device. The capsule material may prevent passage of selected molecular substance(s) and may permit passage of other selected molecular substances, but does not interfere directly with operation of the medical device. One or more selected chemical, optical, electronic, electromagnetic, ultrasound or mechanical signals can be generated externally and passed through the capsule material to activate, deactivate, control or otherwise change the status of the medical device within the cage. Apart from replacement of mis-functioning or non-functioning medical devices and their respective cages from time to time, no further actions are required, other than passage of the selected signal, or sequence of signals, through the capsule material.

Activation of the biological insert can be implemented, for example, using one or more optical or other suitable signals to "awaken" the specialized function of the insert. The optical signal may have one or more wavelengths in the visible, infrared or microwave regions, depending upon the distance of the capsule from an exposed portion of the host body through which the optical signal enters. A timed sequence of non-simultaneous optical signals can be used to raise the energy level of a particular electron or group of electrons to a selected level(s) at which activation occurs. An ultraviolet optical signal can be used for such purpose, if the capsule is located close to an exposed surface of the body, for example, in a skin layer. Until such activation occurs, the biological insert within the capsule is effectively inert. Delivery of one or more selected optical signals can also be used to deactivate an already-active biological insert so that the biological insert can be switched on and off, depending upon need.

Transfer characteristics across a meshwork of CNT material or cell adhesion interactions with the capsule walls can also be modified by inclusion and/or attachment of selected functional groups (e.g., groups involving H, O, N, S, F, Cl, Br, I, a protein, a peptide, a polypeptide, a growth factor, a cytokine, a nucleic acid and/or a nucleic acid polymer) to the CNTs before the capsule is prepared. Some of these functional groups may serve as "markers" in a manner similar to biological markers on a cell membrane, thereby selectively controlling the chemical substances that are transferred across a capsule wall and/or the rate at which such transfer occurs.

The modification can also include adsorption or covalent attachment of specific growth factors, cytokines, antibodies, extracellular matrix proteins or the like. For example, the modification can include covalent attachment of CNTF, polylysine, collagen, fibronectin, laminin, brain-derived neurotrophic factor, ciliary neurotrophic factor, nerve growth factor, forskolin, or inhibitors of myelin-associated glycoprotein and inhibitors of NOGO). If necessary, the adsorption of specific growth factors, cytokines, antibodies, extracellular matrix proteins to the capsule can be stabilized by partial or complete cross-linking of these specific growth factors, cytokines, antibodies, extracellular matrix proteins to one another, rather than by direct binding to the CNT elements of the capsule.

In one approach, the capsules can be prepared from crude preparations of single wall carbon nanotubes ("SWCNTs") synthesized by a laser ablation technique, available from commercial sources. Other preparations of SWCNTs or multiple wall carbon nanotubes ("MWCNTs"), such as those synthesized by the well known HiPCO technique (a high pressure process using carbon monoxide) are also acceptable. The crude preparation is first purified by refluxing in nitric acid for 160 hours and the resulting product is centrifuged, and the pellet is suspended in potassium hydroxide solution (pH=10), then washed twice by centrifugation and re-suspension. The purified CNTs are washed twice in distilled water, using centrifugation and resuspension. The purified CNTs are re-suspended in a suspending medium (e.g., distilled water, or other solvent). The suspended CNTs can be mechanically formed into Bucky paper by removal of water by vacuum filtration over a cellulose filter or similar filter. The suspended CNTs can also be used with the perforated molds as described herein to form 3-dimensional capsules.

Portions of the CNTs incorporated in the capsule produced here may be "bundled", or partially or fully aligned, due to liquid flow through the mesh of CNTs, which may provide a higher than normal density of CNTs in an array. The biocompatible fibers can comprise CNTs, carbon fibers, carbon nanofibers, graphene, graphene flakes, graphene fragments, graphene fibers, or polysaccharides (e.g., bacterial cellulose). The fibers can be randomly oriented or preferentially oriented in the capsule walls. The capsule can comprise fibers of varying composition in one or more distinct layers in the capsule walls. The capsules can incorporate beads into one or more distinct layers in the capsule walls. The capsule can further comprise fibers or beads disposed in the interior of the capsule. The capsule walls have a thickness in a range of 1-100 µm and an area density in a range of 420-1500 µgm/cm².

Bucky paper or capsules as described herein can be prepared having an area density of CNTs in the range of 420-1500 µgm/cm². As shown in inset 101 in FIG. 1, scanning electron microscopy imaging of a portion of the capsule after fabrication demonstrates the fibrous character of the capsule wall. Individual meshwork elements are bundles of carbon nanotubes, and the assembly of fibers into a mesh provides a pore size of approximately 20-1000 nm. Generally, the size can be selected such that cells cannot pass through the pores but the ABS of interest passes freely.

Separate procedures can be utilized for generating and controlling patterns or densities of growth of an array of SWCNTs or MWNTs. Fibers can be grown to a length between about 1 µm and 200 µm, or longer if desired. The length of the fiber can be chosen to provide desired characteristics to the final structure provided. For example, longer fibers may become more entangled to provide a stronger structure, if such is desired. Conversely, shorter fibers may result in a capsule that could be more easily disrupted, if such is desired. During the preparation of the capsule, the fibers form a mesh or mat. The mesh thickness h (mesh) and mesh density partly determine the capsule porosity. A mesh density range of $4 \times 10^6$-$6 \times 10^{10}$ cm² corresponding to a range d=40 nm-5 µm for average nearest neighbor center-to-center separation distance can be produced where a substrate is not used for CNT growth. Use of a higher average thickness h may require use of a higher separation distance d, to preserve similar Bucky paper behavior.

Capsules suitable for implantation can comprise nanotubes, fibers or other filaments in the interior of the capsule, not just as part of the capsule wall. In some embodiments, it may be desirable for CNTs, carbon nanofibers or other filamentous materials to be placed into the interior of the capsule, in order to serve as support scaffolding for the cells and/or tissues that are placed into the scaffold. Including fibers in the capsule interior may promote the growth of cells, influence the differentiation state of cells, or control the 3-dimensional arrangement of the cells within the interior of the capsule.

Capsules can be manufactured with different preparations of CNTs, including CNTs of different lengths, including ultrashort CNTs. Various fiber lengths can also be used to prepare capsules made from carbon nanofibers and other types of filaments.

Capsules can be formed using a plurality of layers, including one or more layers with different types of filaments or fibers, different filament orientation, incorporating different beads, etc. Embodiments of the invention include a wide range of possible filament types in addition to CNTs that could be used to make porous meshwork capsules, to provide a broader range of capsule types and more options for manufacture.

III. Fibers

Capsules can be made of carbon nanotubes, carbon fibers, carbon nanofibers, graphene, graphene flakes, graphene fragments, graphene fibers, or polysaccharide fibers (e.g., bacterial cellulose), or any other filamentous, largely inert material. Many of these materials are well known in the art. For example, the preparation of single wall CNTs is described in U.S. Pat. No. 7,105,596 to Smalley. One advantage of carbon nanofibers and carbon fibers such as those made from CNTs is the relative biological inertness of the material, resulting in biocompatible surfaces which do not provoke immune response from the host immune system.

The fibers can be modified to covalently attach biologically active molecules to provide specific surface reactivity when implanted in the host. For example, CNTs or carbon nanofibers can be treated with acid to open the end of the nanotube, resulting in generation of a reactive carboxylic acid moiety (COOH). The COOH reacts with amines on a desired protein to produce an amide bond, covalently bonding the CNT and protein together. In this way, the CNT can be derivatized or labeled with a desired amine-containing substance (usually a protein).

In addition, as the CNTs are generally staggered in length as they assemble into bundles, the modified ends will also be staggered along the length of a bundle of CNTs. The modified fibers can then present a variety of protein signaling molecules to the host, which may affect the host response to the capsule. For example, the fibers can be modified with inhibitors of T-cells, neutrophils, fibroblasts, macrophages, etc., in order to prevent formation of a fibrous capsule by the host body and thereby prolong the operating life of the delivery system or capsule. The fibers can be modified with additional biomolecules such as growth factors and inhibitors as described above.

IV. Beads

The capsules can incorporate beads in the capsule material or in the capsule interior. "Beads" may include beads, microparticles or nanoparticles, and any or all of these materials can be incorporated into the capsule wall, and beads, microparticles or nanoparticles can be placed into the capsule interior, along with other contents, to impart desired properties to the capsule wall, or to promote desired characteristics of the capsule contents. Beads are typically formed of polymers such as polystyrene or latex, and can be functionalized with biomolecules such as inhibitors or growth factors, as described above. A wide variety of beads are commercially available, and the linkage chemistries for functionalizing the beads are well known in the art. The beads to be incorporated into the capsule wall can be in the range of 100 nm to 5 microns in size so that the beads are retained within the capsule wall.

Beads, microparticles, nanoparticles or other structures entrapped in the capsule wall, or otherwise incorporated into the capsule wall, can be used to facilitate triggering of capsules by externally applied signals, in order that external signals can be delivered to the capsule and received by the capsules to trigger (turn on or turn off) or regulate the capsule wall or its contents, in order to control the functioning of the capsule or its contents, or to cause disintegration of the capsule, or to otherwise render some permanent change to the capsule, to cause it to shut down or to release its contents. Signals may include microwave signals; other E/M radiation, particle radiation, such as proton radiation or heavy ion radiation, and ultrasound signals.

Embodiments of the invention make possible the incorporation of a wide range of beads to augment the functionality of the carbon meshwork capsules. The incorporation of beads could be accomplished by entangling beads in the fiber meshwork during manufacture of the capsule, sandwiching beads between layers of the fiber meshwork during manufacture of the capsule, or covalently or noncovalently attaching beads to the CNTs or other mesh elements. The incorporation of beads into the structure of the capsule takes advantage of a growing range of bead and particle types that could easily be incorporated into the capsule.

Beads, microparticles or nanoparticles can be designed to be sensitive to radiation, including electromagnetic radiation (including visible light, UV light, X-rays, gamma rays, IR waves, microwaves, etc.) or particle radiation (protons, heavier elements) or magnetic fields, so that an external "signal" could be delivered to the capsules, once implanted into the body to trigger the capsule, to turn on, turn off, or otherwise regulate the action of the contents of the capsule, or to regulate the properties of the capsule wall, or even to cause destruction (e.g., loss of integrity) of the capsule or its contents, if such was desired. The advantage is that the capsules containing cells, tissues or medical devices can be made to operate autonomously, by being sensitive to external signals that would trigger appropriate events inside the capsule; or, signaling/triggering could be used to tailor the functioning of the capsule contents deliberately, to respond to changing circumstances of the host (recipient) or to changing circumstances of the host environment.

In some embodiments, the beads can comprise radio-opaque markers such as metals. The use of radio-opaque substances in beads can provide a means for localizing or visualizing a capsule after it is implanted within a host. Metals that are useful for localizing a capsule preferably include nonferrous metals that are compatible with computed tomography or magnetic resonance imaging in a patient. Typical metals would include gold or titanium.

In some embodiments, the beads can comprise radioactive substances that emit ionizing radiation. The ionizing radiation can be used as a marker for the location of the capsule. Alternatively, or in addition, the ionizing radiation can be used as a treatment protocol for disease, for example, for localized treatment of cancer or other growth. For localizing a capsule or for local treatment, typically the radioactive substance includes gamma emitting radionuclides and would be secured within the capsule so that it does not diffuse out of the capsule and penetrate throughout the patient's body.

V. Methods of Preparing Capsules

The methods provide an efficient and practical way to form biocompatible fibrous capsules in the form of a 3-dimensional CNT meshwork, to serve as containers for cells and/or tissues, to serve as containers for medical devices, or to serve as repositories of other active substances. The methods can facilitate the implantation of these cells, active substances or medical devices into a host recipient. The use of CNT meshwork for these applications serves generally to provide a shield or barrier between the transplanted/implanted items, such that the host immune system cannot interact with the contents within the CNT meshwork container. Without the "immune shield," the host immune system could trigger an undesirable immune response (including but not limited to a rejection response, or an acute or chronic inflammatory reaction) directed against the transplanted/implanted items.

The methods can comprise providing a perforated mold, immersing the perforated mold into a suspension of biocompatible fibers in a suspending medium, withdrawing the suspending medium through the perforated mold such that the fibers form a tangled mesh around the outside and conform to the shape of the perforated mold, and removing the perforated mold to produce a biocompatible capsule component, and sealing the capsule. The sealing comprises forming at least one region of overlap where two regions of capsule wall are in intimate contact, and pressing the two regions of capsule wall together such that the capsule wall surfaces are bound by van der Waals forces and/or entanglement of the biocompatible fibers. When sealed, the capsule interior is substantially isolated from the medium surrounding the capsule, except for diffusion of at least one species of molecule between the capsule interior and the ambient medium.

The methods can further comprise providing a plurality of molds to prepare a plurality of capsule components, and assembling the plurality of capsule components to form an enclosed 3-dimensional capsule. Withdrawing the suspending medium can be provided by applying positive pressure to the outside of the perforated mold or by applying negative pressure to inside of the perforated mold.

The methods can further comprise inserting a plurality of cells into the capsule before assembling the capsule components together. The methods can further comprise inserting a medical device into the capsule before assembling the capsule components together.

The methods can further comprise inserting a source of one or more active biological substances into the capsule before assembling the capsule components together. The active biological substance can include pharmaceutically active agents, chemotherapeutic agents, radio-labeled active agents, peptides, proteins, growth factors, cytokines, growth inhibitors, polynucleotides, and the like, without limitation.

In some embodiments, the source of active biological substances is a plurality of cells, wherein the plurality of cells releases the one or more active biological substances such that the one or more active biological substances are free to diffuse across the capsule walls.

In some embodiments, the source of active biological substances is a composition comprising one or more active biological substances, wherein the composition releases the one or more active biological substances such that the one or more active biological substances are free to diffuse across the capsule walls. The composition can be a sustained release composition.

In some embodiments, the source of active biological substances is a medical device providing the controlled release of one or more active biological substances, wherein the composition releases the one or more active biological substances such that the one or more active biological substances are free to diffuse across the capsule walls.

The biocompatible fibers can comprise carbon nanotubes, carbon fibers, carbon nanofibers, graphene, graphene flakes, graphene fragments, graphene fibers, or polysaccharides (e.g., bacterial cellulose). The methods can further comprise orienting the fibers as the capsule components are formed. The methods can further comprise incorporating different fibers into one or more distinct layers as the capsule components are formed. The methods can further comprise incorporating beads into one or more distinct layers as the capsule components are formed. The methods can further comprise incorporating fibers into the interior of the capsule components to form an interior scaffold before sealing the capsule. The methods can further comprise incorporating beads into the interior of the capsule before sealing the capsule.

Figure 3:
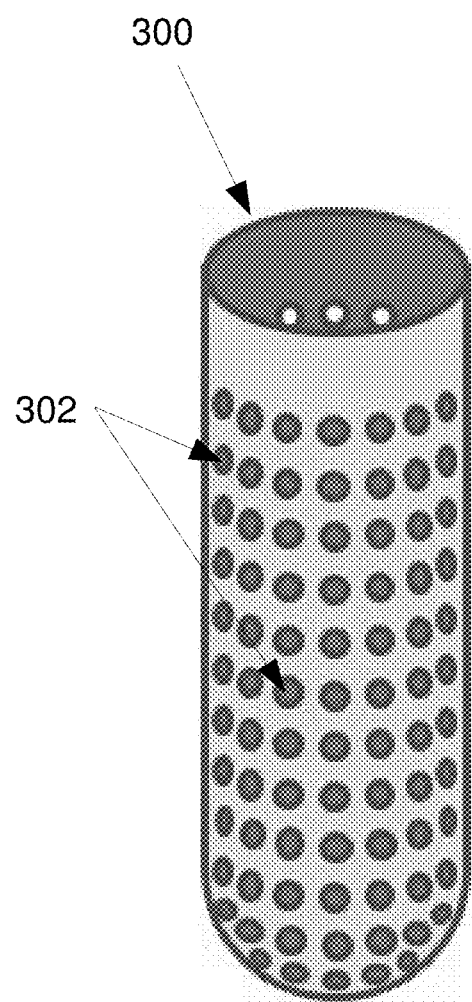
FIG. 3 illustrates an embodiment of a mold for forming a capsule.

Embodiments of the invention include methods for creating 3-dimensional containers (capsules) made of biocompatible fibers by use of a perforated mold. The shape and dimensions of the mold determine the shape and dimensions of the capsule. The molds can be generally tubular in form, made of a rigid material, with perforations (holes or pores), and are designed to be immersed into a suspension of biocompatible fibers (e.g., carbon nanotubes, "CNTs") dispersed in a suspending medium such as a solvent (e.g., acetone) or other liquid such as water with added surfactant. The perforations provide a way to remove the solvent from a suspension of fibers, such that the fibers are deposited onto the surface of the mold, forming a meshwork with an overall 3-dimensional shape that is determined by the 3-dimensional shape of the mold. For example, a cylindrical mold 300 with a round bottom can be used to form a cylindrical container with a round bottom (as shown in the FIG. 3). The perforations 302 in the rigid mold permit fluid or liquid to pass from the exterior to the interior of the mold, but are sized to prevent fibers (e.g., CNTs or bundles of CNTs) from passing through the perforations.

Figure 4:
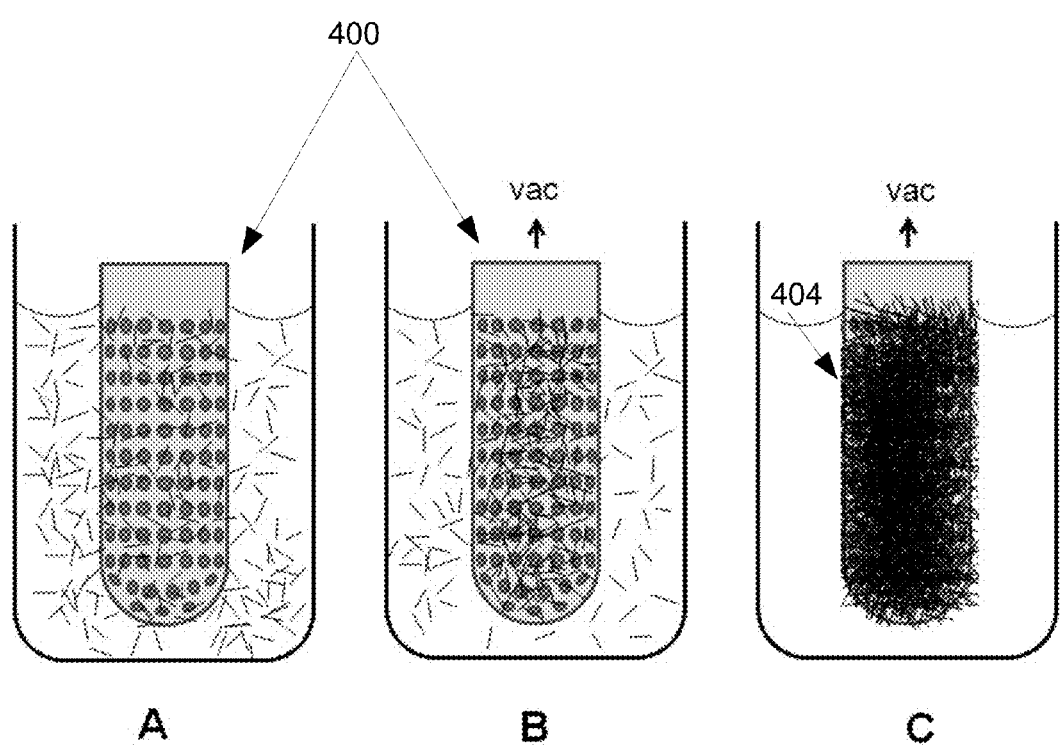
FIG. 4 illustrates one embodiment of the sequence of events in the preparation of capsules.

As shown in FIG. 4, the perforated mold 400 is placed into a suspension of CNTs (panel A) and the mold is secured to a vacuum source (not shown). The suspending medium is withdrawn by applying a vacuum to the inside of the cylindrical mold, so that suspending medium is drawn through the mold, carrying CNTs to the surface of the mold (panel B). The perforations of the mold are sized to prevent passage of the CNTs into the interior of the mold, so that that the CNTs accumulate at the surface of the mold, where they become entangled with each other to form a meshwork. With continued application of a vacuum to the interior of the mold, more and more of the suspending medium is withdrawn, resulting in increasing deposition of CNTs to the outside of the mold, resulting in increasing thickness of the CNT 404 meshwork (panel C). Additional CNTs and/or suspending medium can be added to the suspension as desired to continue the process.

Figure 5:
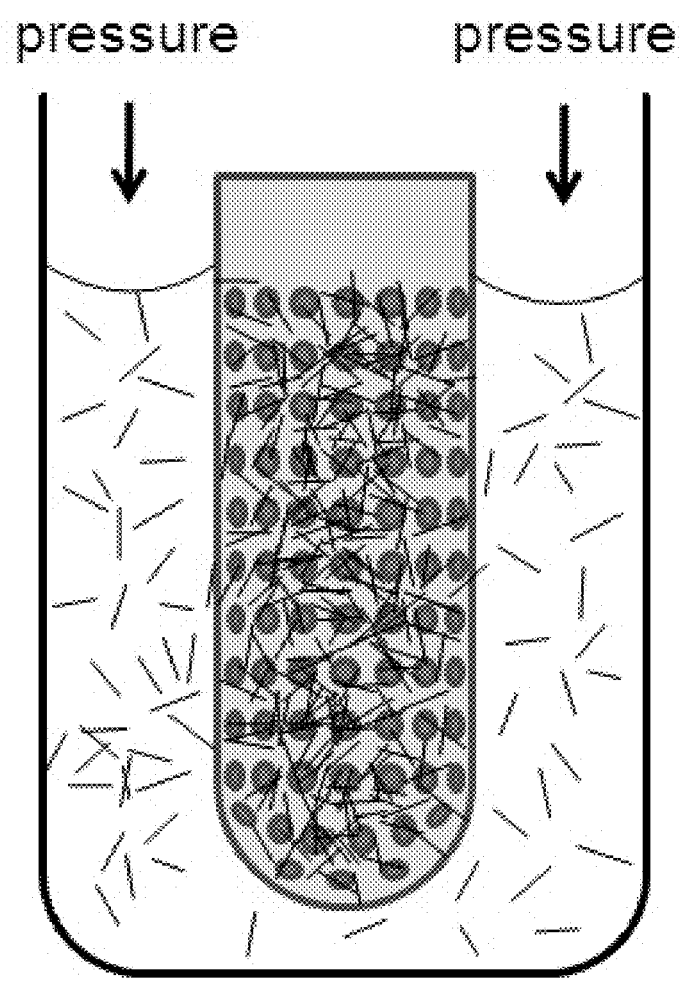
FIG. 5 illustrates one embodiment of the sequence of events in the preparation of capsules.

In another embodiment, instead of using a vacuum to draw the suspending medium through the perforations of the mold, pressure can be applied to the exterior to the mold, and the interior of the mold left at atmospheric pressure (FIG. 5). With this variation, the difference in pressure between the interior of the mold and the exterior of the mold can be greater than with use of vacuum, which can be used to speed the rate at which suspension fluid is forced through the perforations (holes or pores) of the mold.

Figure 6:
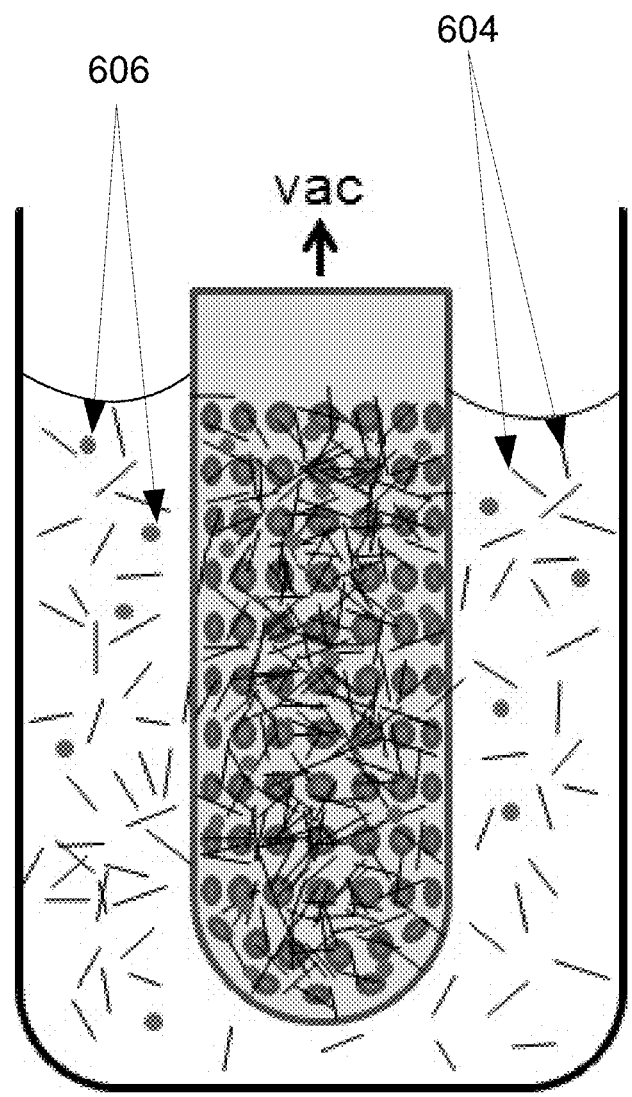
FIG. 6 illustrates one embodiment of the sequence of events in the preparation of capsules incorporating beads.

In some embodiments, beads can be added to the fiber meshwork during the manufacturing process. Beads 606 can be added to the suspension of fibers 604, so that as the fluid phase is drawn into the interior of the perforated mold (e.g., by vacuum or pressure), the beads become entrapped in the growing meshwork (shown schematically in FIG. 6). Alternatively, the beads can be added to the suspension after a layer of CNTs is deposited, resulting in the incorporation of a layer of beads after the first layer of CNTs is formed, so that the beads are not exposed to the interior of the resulting CNT meshwork capsule. The layer of beads can then be covered by depositing another layer of CNT or other fiber meshwork if desired.

Different beads with different functionalities can be incorporated into one or more separate layers of the container, if desired. The use of layered construction can be used to position some beads closer to the interior of the resulting capsule, and some beads closer to the exterior, where distinct functionalities of the interior versus the exterior of the capsule are desired. Modified CNTs can also be incorporated into one or more layers of the capsule during the manufacturing process.

A scaffold of fibers (e.g., CNTs, carbon fibers or graphene fibers) can also be placed into the interior of the capsule, to serve as a support for the growth of cells, typically after the capsule has been formed. The fibers are suspended in solvent or aqueous solution with surfactant in a concentration range of one microgram per ml to 100 mg per ml (a higher concentration than that used to form the capsule). The suspension is added to the capsule interior and as the solvent or surfactant is removed, the fibers form bundles that create a scaffold of fibers crossing the interior of the capsule. The advantage is that cell or tissue growth in the capsule could be enhanced or optimized, so that more efficient biological effects can be achieved once implantation takes place, including longer useful lifespan of the contents of the capsule, or more reliable functioning of the contents of the capsule. For use as a scaffold for growth of cells or support of implanted tissue, the fibers in the interior of the capsule are provided typically at less than one percent of the interior volume of the capsule.

Figure 7:
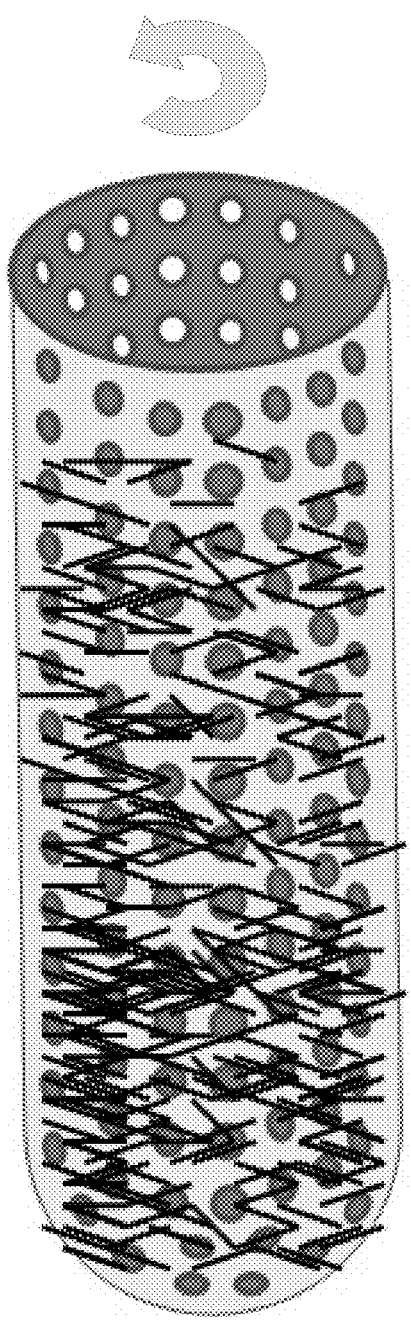
FIG. 7 illustrates one embodiment of the sequence of events in the preparation of capsules.

Various techniques can be used to influence or control the orientation of the CNTs, nanofibers or filaments in the manufacture of the capsules. For example, the mold can be rotated or moved vertically with respect to the CNT suspension during the deposition process. The use of directed flow, or stirring of the suspension can also affect the orientation of the fibers in the final capsule. The rotation of the mold is depicted schematically in FIG. 7. It can be seen that the majority of the CNTs are generally oriented with the direction of rotation rather than exhibiting a random distribution of orientations.

Figure 8:
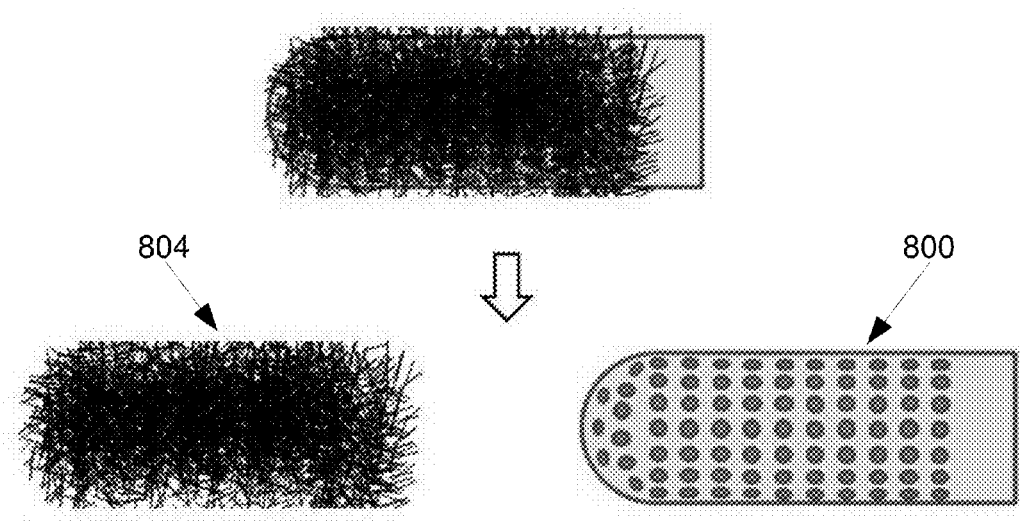
FIG. 8 illustrates one step in the sequence of events in the preparation of capsules.

After the capsule formation is complete, the mold 800 can be removed, leaving behind the CNT meshwork 804, still holding the shape of the mold, as shown in FIG. 8. The capsule can be dried to remove suspending medium and stored prior to use.

Figure 9:
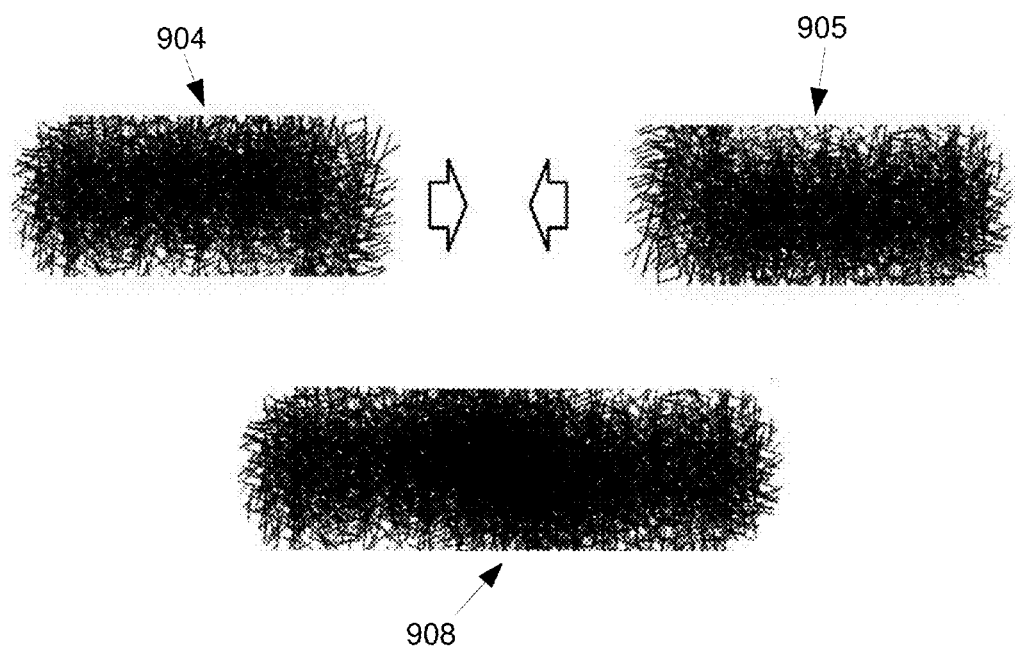
FIG. 9 illustrates one step in the sequence of events in the preparation of capsules.

In one embodiment, two capsule portions can be created where the outside diameter of one capsule portion is approximately equal to the inside diameter of the other capsule portion, and a "complete" capsule is formed by taking the two capsule portions and joining them together by inserting the open end of the smaller capsule portion into the open end of the larger capsule portion, overlapping the open ends. For example, two capsule "halves" 904 and 905 can be formed and assembled by inserting the open end of one half capsule into the other to form a closed capsule 908. This embodiment is shown schematically in FIG. 9. The capsule is sealed by non-covalent association between capsule halves (the CNTs are attracted to one another by van der Waals forces), and entanglement of fibers at the mating capsule portion surfaces to hold the complete capsule together. The two portions of capsule can have the same or different shapes and dimensions, so long as the overlapping portions come into close contact.

Other methods of sealing the capsules will be readily apparent to those of skill in the art. For example, the capsule having one open end as depicted in FIG. 8 could be sealed shut by pinching the top portion closed, or contacting the open end with some other capsule of suitable shape, or contacting it with a suitable shape and thickness of Bucky paper. The CNTs can non-covalently associate and entangle to close the capsule. Any method of closing the capsule can be used so long as the fiber entanglement is preserved.

Figure 10:
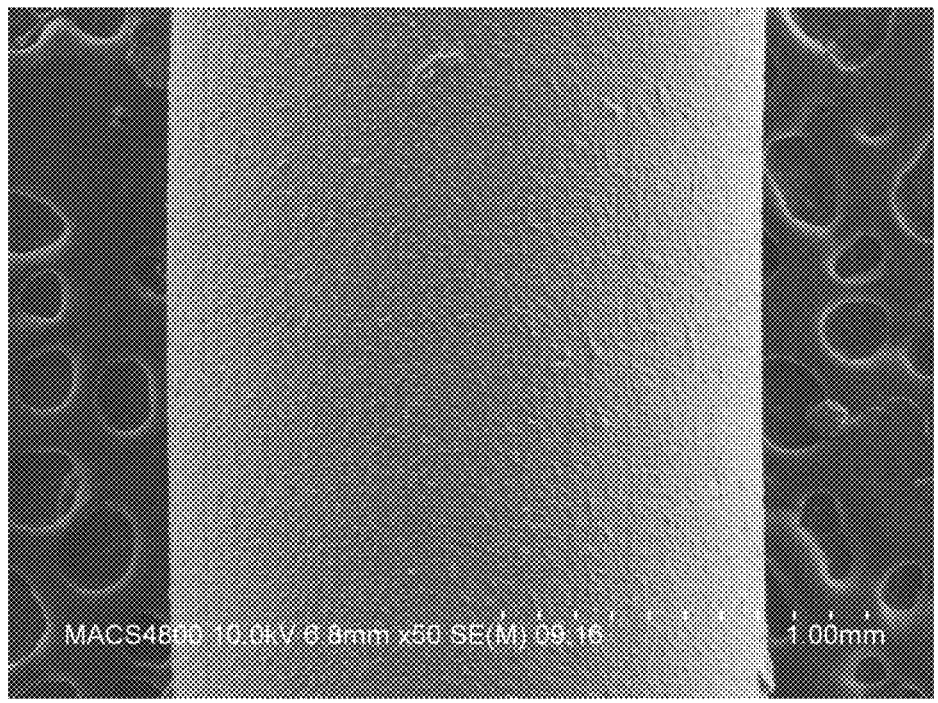
FIG. 10 shows a scanning electron micrograph of a cylindrical capsule after manufacture.

The finished capsule demonstrates a smooth, uniform surface of CNT meshwork, as shown using low power scanning electron micrograph (FIG. 10). The width of the cylinder shown in FIG. 10 is approximately 1.5 mm.

In another embodiment, the mold can have an oval cross-section and no perforations in the end cap. A tube with an oval cross-section can be formed on the mold and then removed from the mold. The aspect ratio of the oval dimension can be from about 2:1 to about 20:1 (a circular shape has an aspect ratio of 1:1). In these embodiments, a capsule can be formed by pressing the ends together along a length to seal the ends of the tube. Typically the seal length can be at least equal to the long axis of the oval. No additional fastening aids such as glue, stitching, or clamps are required, and only a single molded component is required to form an enclosed and sealed container. Instead, the ends of the capsule can be pinched together to seal the two capsule wall surfaces together. Under conditions of close proximity, the wall surfaces are attracted due to the van der Waals forces between the CNTs. Sealing can also be effected by placing the walls in proximity while contacting the walls with aqueous solution, whereby the CNT ends are able to entangle with the CNT ends from the adjacent wall without being damaged (changing density or porosity).

For example, an oval tube having an aspect ratio of 5:1 has been used with good result. Depending on the particular choice of fibers, wall thickness, and fiber density, the finished capsule wall will have a limiting flexibility. Actions which try to bend the wall material past a limiting strain point will cause fiber breakage that can affect the integrity of the capsule wall. Typical example tubes made at an aspect ratio of 5:1 can be sealed by pressing the ends together without significant fiber breakage, and good end seals having no measureable leakage of cells from a capsule interior can reliably be made. To optimize entanglement, it is generally desirable to avoid sheer forces which can break fibers. The two surfaces should be pressed firmly together in a manner which does not cause the mating surfaces to slide relative to each other.

VI. Advantages and Applications

The capsules utilize materials that have not yet been used extensively in biological applications. These materials provide biocompatibility and the potential to permit or block the passage of various substances across the capsule by controlling the porosity of the capsule wall. These materials also provide an ease of use and wide variety of shapes into which the material can be shaped, and an ability to control the dimensions of a capsule made from the material. The capsules provide a micro-environment in which cells can grow, cell differentiation can be promoted or suppressed and cells and tissues can be transplanted. In addition, secretion, sensing and monitoring of chemical substances present can be performed, without the need for, or with limited need for, use of immunosuppressive drugs or other special precautions.

Because the 3-dimensional structures are not assembled from flat pieces of pre-formed Bucky paper, fewer seams are required, and therefore there is less chance that the containers could leak or rupture or otherwise fail to keep the contents fully shielded from the host immune system and other host factors that could damage the contents, or allow the contents to escape from the containers.

The method of manufacture of these 3-dimensional structures by use of a perforated mold provides potentially more variation in the range of shapes of the CNT meshwork structures.

No suture or other ligature material is needed to create a fully closed container, which simplifies the process of preparing and loading the containers, and potentially minimizes the chance of an immune reaction that could be caused by the suture or ligature, specifically, because the suture or ligature may not be as biocompatible as the carbon nantube meshwork. The elimination of non-carbon closure materials (that could cause an unwanted host immune response after implantation into the body) can improve the biocompatibility of the capsule.

The methods can be scaled up to provide for large-scale production of these 3-dimensional CNT meshwork structures, for efficient manufacture, with minimal manual intervention compared to manufacture of containers built up from flat pieces of Bucky paper.

Nanotube, filament or fiber orientation can be controlled, to optimize the physical properties of the capsule and optimize the pore size or pore size distribution, providing more precise control of the properties of the capsule. The advantage is more precise control of the properties of the capsule.

The manufacturing methods provide for efficient means for controlling the orientation of the CNT meshwork structural elements (single-walled CNTs, multi-walled CNTs, or bundles of single-walled or multi-walled CNTs), for example, by varying the alignment of fibers, which may impart advantageous structural and/or mechanical characteristics to the CNT meshwork structures.

The manufacturing methods make possible the formation of CNT meshwork structures comprised of multiple layers, where layers with different properties may be desirable. For example, an inner layer may be selected or modified to have certain properties to optimize the interaction of the contents of the container with this layer, and an outer layer may be selected or modified to optimize the interaction of this layer with the surrounding tissue, medium or cells.

The manufacturing methods make possible the incorporation of beads into the CNT meshwork capsule, where the beads may be used to impart some added functionality to the CNT meshwork. The beads may be confined to the space between distinct layers of CNT meshwork, and different types of beads with different functionalities may be used, each confined to its own layer.

It is to be understood that while the invention has been described in conjunction with the preferred specific embodiments thereof, that the description above as well as the examples that follow are intended to illustrate and not limit the scope of the invention. The practice of the present invention will employ, unless otherwise indicated, conventional techniques of organic chemistry, pharmaceutical chemistry, immunochemistry, biochemistry and the like, which are within the skill of the art. Other aspects, advantages and modifications within the scope of the invention will be apparent to those skilled in the art to which the invention pertains. Such techniques are explained fully in the literature.

All patents, patent applications, and publications mentioned herein, both supra and infra, are hereby incorporated by reference in their entireties for all purposes.

EXAMPLES

Example 1

Islet Cells Encapsulated in a Capsule for Treatment of Diabetes

A capsule is prepared in two complementary halves from CNTs having dimensions of approximately 1 mm by 10 mm. Islet cells (harvested from donors) are added to one half of the capsule in an amount of from about $10^6$ to about $10^7$ cells, along with solution containing appropriate growth medium, and the capsule is assembled by inserting the complementary capsule half. The capsule is implanted in a patient under the skin. The cells within the capsule are nourished by the extracellular fluids of the patient's body, and can respond to glucose which diffuses across the pores of the capsule. The islet cells produce insulin in response to elevated glucose, which diffuses out of the capsule across the pores, and into the blood stream of the patient, thereby providing a supplemental source of insulin for controlling blood glucose levels. Because the islet cells automatically respond to elevated glucose and cease to generate insulin when glucose levels fall, the capsule provides an in situ insulin delivery system capable of controlling blood glucose in a patient in need thereof.

Example 2

Acute Response Treatment of Radiation Exposure

A capsule is prepared in two complementary halves from CNTs having dimensions of approximately 1 mm by 10 mm. Cells (prokaryotic or eukaryotic, obtained from cultures of cells or harvested from donor animals) are genetically engineered to produce granulocyte colony stimulating factor (G-CSF) and can respond to a trigger such as an antibiotic resistance gene engineered into the cells to release G-CSF, or can respond to the radiation exposure itself. When acute radiation exposure has occurred, the trigger (e.g., antibiotic) can be administered, thereby causing the cells in the capsule to produce and release G-CSF. The cells are added to one half of the capsule in an amount of from about $10^6$ to about $10^7$ cells, along with solution containing appropriate growth medium, and the capsule is assembled by inserting the complementary capsule half. The capsule is implanted in a patient under the skin. The cells within the capsule are nourished by the extracellular fluids of the patient's body, and respond to the trigger to release G-CSF, which diffuses across the pores of the capsule. The G-CSF diffuses into the blood stream of the patient, thereby providing a supplemental source of G-CSF for controlling levels of blood cells. Because the cells respond to the trigger and cease to generate G-CSF when levels of the trigger molecule fall, the capsule provides an in situ G-CSF delivery system capable of stimulating blood cell growth and replenishment in a patient suffering from acute radiation exposure.

Example 3

Cells Encapsulated in a Capsule for Gene Therapy

A capsule is prepared in two complementary halves from CNTs having dimensions of approximately 1 mm by 10 mm. Cells (prokaryotic or eukaryotic, obtained from cultures of cells or harvested from donor animals) genetically engineered to produce factor VIII or IX are added to one half of the capsule in an amount of from about $10^6$ to about $10^7$ cells, along with solution containing appropriate growth medium, and the capsule is assembled by inserting the complementary capsule half. The capsule is implanted in a patient under the skin. The cells within the capsule are nourished by the extracellular fluids of the patient's body, and produce clotting factors which diffuse across the pores of the capsule. The cells produce clotting factors at a constant rate, which diffuse out of the capsule across the pores, and into the blood stream of the patient, thereby providing a supplemental source of clotting factors for controlling blood clotting. The capsule provides an in situ delivery system capable of controlling blood clotting in a patient in need thereof.

Example 4

Antibody Producing Cells Encapsulated in a Capsule for Treatment of Cancer

A capsule is prepared in two complementary halves from CNTs having dimensions of approximately 1 mm by 10 mm. Cells (prokaryotic or eukaryotic, obtained from cultures of cells or harvested from donor animals) genetically engineered to produce anti-tumor antibodies are added to one half of the capsule in an amount of from about $10^4$ to about $10^8$ cells, along with solution containing appropriate growth medium, and the capsule is assembled by inserting the complementary capsule half. The capsule is implanted in a patient near the site of a tumor. The cells within the capsule are nourished by the extracellular fluids of the patient's body, and produce antibodies which diffuse across the pores of the capsule. The cells produce antibodies at continuously, which diffuse out of the capsule across the pores, into the vicinity of the tumor in the patient, thereby providing a localized source of anti-tumor antibodies for treating cancer.

The capsule provides an in situ delivery system capable of providing antibodies in a patient in need thereof.

Example 5

Chemotherapeutic Agents Encapsulated in a Capsule for Treatment of Cancer

A capsule is prepared in two complementary halves from CNTs having dimensions of approximately 1 mm by 10 mm. A sustained release composition comprising an anthracycline, or cytosine arabinoside, or a combination thereof, is inserted into one half capsule, and the capsule is assembled by inserting the complementary capsule half. The capsule is implanted in a patient near the site of a tumor. The sustained release composition provides chemotherapeutic agents that diffuse across the pores of the capsule. The chemotherapeutic agent(s) diffuse out of the capsule across the pores, and into the vicinity of the tumor in the patient, thereby providing a high localized concentration of chemotherapeutic agents to treat the cancer. The capsule provides an in situ delivery system capable of providing localized delivery of chemotherapeutic agents in a patient in need thereof.

What is claimed is:

1. A method for preparing a biocompatible capsule comprising:
   providing a perforated mold,
   immersing the perforated mold into a suspension of biocompatible fibers in a suspending medium,
   withdrawing the suspending medium through the perforated mold such that the fibers form a tangled mesh around the outside of the perforated mold and conforming to the shape of the perforated mold,
   removing the perforated mold to produce a first biocompatible capsule component,
   producing a second biocompatible capsule component,
   sealing the first and second biocompatible capsule components to form the capsule;
   wherein the sealing comprises
      forming at least one region of overlap between the first and second capsule components where the fibers of the at least one overlap region are in intimate contact,
      pressing the at least one overlap region together such that the fibers of the at least one overlap region are bound by van der Waals forces, and
      forming a smooth, uniform surface of fibers along the exterior surface of the capsule, and
   wherein the interior of the capsule is substantially isolated from the medium surrounding the capsule, except for diffusion of at least one species of molecule between the capsule interior and the ambient medium.

2. The method of claim 1, wherein the withdrawing is provided by at least one of applying positive pressure to the outside of the perforated mold and applying negative pressure to the inside of the perforated mold.

3. The method of claim 1, further comprising providing a plurality of perforated molds to form a plurality of fibrous capsule components, and assembling the plurality of fibrous capsule components together to form an enclosed 3-dimensional capsule, wherein two fibrous capsule components are of different diameters such that an open end of the capsule component with a smaller diameter is inserted into an open end of the capsule with a larger diameter to form an overlap region where the fibers are attracted to one another by van der Waals forces.

4. The method of claim 1, further comprising inserting a plurality of cells into the capsule before sealing the capsule.

5. The method of claim 1, further comprising inserting a medical device into the capsule before sealing the capsule.

6. The method of claim 1, wherein the biocompatible fibers include at least one of carbon nanotubes, carbon fibers, carbon nanofibers, graphene, graphene flakes, graphene fragments, graphene fibers, and polysaccharides.

7. The method of claim 1, further comprising orienting the fibers as the capsule is formed.

8. The method of claim 1, further comprising incorporating different fibers into one or more distinct layers as the capsule is formed.

9. The method of claim 1, further comprising incorporating beads into one or more distinct layers of the fibers as the capsule is formed.

10. The method of claim 1, further comprising incorporating fibers into the interior of the capsule to form an interior scaffold before sealing the capsule.

11. The method of claim 1, further comprising incorporating beads into the interior of the capsule before sealing the capsule.

* * * * *